(12) United States Patent
Lu

(10) Patent No.: US 11,246,798 B2
(45) Date of Patent: Feb. 15, 2022

(54) HANDHELD MULTI-TIP SCRAPING AND MOXIBUSTION DEVICE

(71) Applicant: Fan Lu, Guangdong (CN)

(72) Inventor: Fan Lu, Guangdong (CN)

( * ) Notice: Subject to any disclaimer, the term of this patent is extended or adjusted under 35 U.S.C. 154(b) by 299 days.

(21) Appl. No.: 16/073,295

(22) PCT Filed: Jan. 24, 2017

(86) PCT No.: PCT/CN2017/072304
§ 371 (c)(1),
(2) Date: Nov. 6, 2018

(87) PCT Pub. No.: WO2017/129104
PCT Pub. Date: Aug. 3, 2017

(65) Prior Publication Data
US 2019/0076318 A1 Mar. 14, 2019

(30) Foreign Application Priority Data
Jan. 27, 2016 (CN) .......................... 201620081166.5

(51) Int. Cl.
*A61H 39/06* (2006.01)
*A61H 39/04* (2006.01)
(Continued)

(52) U.S. Cl.
CPC ............ *A61H 39/06* (2013.01); *A61F 7/0053* (2013.01); *A61F 7/034* (2013.01); *A61H 7/00* (2013.01);
(Continued)

(58) Field of Classification Search
CPC .................... A61H 39/06; A61H 39/04; A61H 39/08–086; A61H 7/00; A61H 7/003;
(Continued)

(56) References Cited

U.S. PATENT DOCUMENTS 1,831,669 A * 11/1931 Kono ...................... A61B 18/06
604/24
3,946,733 A * 3/1976 Han ....................... A61M 35/30
604/24
(Continued)

FOREIGN PATENT DOCUMENTS

CN 1116921 A 2/1996
CN 2315951 Y 4/1999
(Continued)

OTHER PUBLICATIONS

International Search Report dated Mar. 30, 2017, from the ISA/CN, for International Patent Application No. PCT/CN2017/072304 (filed Jan. 24, 2017), 8 pages.
(Continued)

*Primary Examiner* — Justine R Yu
*Assistant Examiner* — Kelsey E Baller
(74) *Attorney, Agent, or Firm* — Ascenda Law Group, PC

(57) ABSTRACT

A handheld multi-tip scraping and moxibustion device, including: pushing and scraping air-guiding tips distributed on a panel each having a through-cavity; and a moxa burning chamber communicating with the through-cavity to enable heat and air in the moxa burning chamber to be discharged gradually for use through the pushing and scraping heat-conducting and air-guiding tips. The pushing and scraping air-guiding tips including a first set of pushing and scraping heat-conducting and air-guiding tips located in a middle portion of the panel and a second set of pushing and scraping heat-conducting and air-guiding tips located around the first set of pushing and scraping air-guiding tips, wherein the height of the first set of pushing and scraping heat-conducting and air-guiding tips is less than the height of the second set of pushing and scraping heat-conducting and air-guiding tips in order to form a multi-layered stepped air discharge.

12 Claims, 4 Drawing Sheets

(51) Int. Cl.
  *A61F 7/00* (2006.01)
  *A61F 7/03* (2006.01)
  *A61H 7/00* (2006.01)

(52) U.S. Cl.
  CPC ............. *A61H 7/002* (2013.01); *A61H 7/003* (2013.01); *A61H 39/04* (2013.01); *A61F 7/00* (2013.01); *A61F 2007/006* (2013.01); *A61H 2201/0153* (2013.01); *A61H 2201/0157* (2013.01); *A61H 2201/025* (2013.01); *A61H 2201/102* (2013.01); *A61H 2201/1253* (2013.01); *A61H 2201/169* (2013.01)

(58) Field of Classification Search
  CPC ............. A61H 7/002; A61H 2201/169; A61H 2201/1253; A61H 2201/0153; A61H 2201/102; A61H 2201/025; A61F 7/034; A61F 7/00; A61F 2007/006; A61B 18/06; A61B 2018/064
  USPC .......................................................... 601/15
  See application file for complete search history.

(56) References Cited

U.S. PATENT DOCUMENTS

| | | | | |
|---|---|---|---|---|
| 4,203,438 A | * | 5/1980 | Shiu | A61B 18/06 604/24 |
| 4,731,050 A | * | 3/1988 | Harada | A61H 39/04 604/24 |
| 5,405,310 A | * | 4/1995 | Yoo | A61H 39/04 601/134 |
| 5,904,664 A | * | 5/1999 | Kim | A61M 37/00 604/19 |
| 5,931,806 A | * | 8/1999 | Shimada | A61H 39/06 604/24 |
| 6,783,508 B1 | * | 8/2004 | Wells | A61H 39/02 604/24 |
| 9,044,376 B2 | * | 6/2015 | Sun | A61H 39/06 |
| 9,125,481 B2 | * | 9/2015 | Watanabe | A61H 7/003 |
| 9,320,679 B2 | * | 4/2016 | Lee | A61H 39/06 |
| 2006/0276730 A1 | * | 12/2006 | Thiebaut | A61H 7/003 601/112 |
| 2013/0281894 A1 | * | 10/2013 | Ling | A61H 15/00 601/19 |
| 2017/0087005 A1 | * | 3/2017 | Na | A61H 39/06 |
| 2018/0207060 A1 | * | 7/2018 | Wang | A61F 7/032 |

FOREIGN PATENT DOCUMENTS

| | | | |
|---|---|---|---|
| CN | 202207289 U | 5/2012 | |
| CN | 104138329 A | 11/2014 | |
| CN | 204744939 U | 11/2015 | |
| CN | 105534699 A | 5/2016 | |
| CN | 205515525 U | 8/2016 | |
| KR | 200476037 Y1 | 1/2015 | |
| WO | WO-2007024060 A1 * | 3/2007 | ............. A61H 39/06 |

OTHER PUBLICATIONS

Written Opinion dated Mar. 30, 2017, from the ISA/CN, for International Patent Application No. PCT/CN2017/072304 (filed Jan. 24, 2017), 5 pages.

International Preliminary Report on Patentability dated Jul. 31, 2018, from the International Bureau of WIPO, for International Patent Application No. PCT/CN2017/072304 (filed Jan. 24, 2017), 15 pgs.

Written Opinion dated Mar. 30, 2017, from the ISA/CN, for International Patent Application No. PCT/CN2017/072304 (filed Jan. 24, 2017), English Translation, 8 pages.

* cited by examiner

HANDHELD MULTI-TIP SCRAPING AND MOXIBUSTION DEVICE

RELATED APPLICATIONS

This application is a National Stage under 35 USC 371 of and claims priority to International Application No. PCT/CN2017/072304, filed 24 Jan. 2017, which claims the priority benefit of CN Application No. 201620081166.5, filed 27 Jan. 2016.

FIELD OF THE INVENTION

The present invention relates to a handheld multi-tip scraping and moxibustion device.

BACKGROUND

A combination of thermal therapy and aromatherapy, moxibustion is a treasure from China that has been shared with the world. Due to limitations of the existing tools thereof, its functions have not been fully utilized. Moxibustion produces a therapeutic effect by applying heat energy together with moxa smog containing wormwood oil to the body surface, the moxa smog being indispensable in the treatment. An excessive spreading of moxa smog, however, may cause discomfort.

The functions of scraping therapy comprising blood dredging, diaphoresis and activation of collaterals are combined with moxibustion according to the present invention so as to produce a new therapy: scraping and moxibustion. With the ability to aid the healing of pulled muscle, pulled tendon after exercise, and the muscle rigidity caused by long-term accumulation of muscle injuries, the scraping and moxibustion are derived from a breakthrough application from Eastern medicine, and is safer, easier, and more efficient in the repair of muscle, as compared to currently known muscle repair methods. The scraping and moxibustion enables injured muscle and tendon to heal in a very short period of time, which can be of great assistance to athletes who participate in competitive sports. The repair process occurs through a natural relaxation process, and after the repair process, there is no sequelae, such as muscle aches and rigidity in the affected area, as may be encountered by other treatment methods.

The head is the human body's command and main embodiment of appearance, and brain health is the most important part of human health. The vertex extrameridian acupoint of the human body (Sishengcong acupoint) has a special effect on mental illness, and has an amazing adjustment effect on psychosis, vascular dementia and other serious illnesses. The problem on how to effectively transport the heat energy and moxa smog of the moxibustion to the acupoints and collaterals below an individual's hair without damaging his/her hair has previously not been solved, and the invention of the handheld multi-tip scraping and moxibustion device solves this problem. The fixed acupoint moxibustion is available, especially the moxibustion to five acupoints of Baihui and Sishencong at the same time. When the fixed acupoint moxibustion is conducted, the scraping and moxibustion device is fixed by an elastic tape to the individual, allowing the individual to walk as usual, Alternatively, the scraping and moxibustion device can also be held as a comb to conduct the scraping and moxibustion to the vertex and face. The searching of collaterals, scraping and moxibustion can be conducted throughout the body, and the therapeutic effects can be quite amazing. The heat energy and the moxa smog are transmitted to the skin through the tip (more specifically by a through-cavity internally provided within the tip), and the heat energy makes the patient feel pleasant and comfortable when the scraping and moxibustion are performed. Moreover, various aromatherapy essential oils can also be evaporated separately to conduct the pioneering aromatherapy scraping therapy. In the invention, an enclosure cloth may be used to wrap the scraping and moxibustion device such that only a tip surface is exposed. The enclosure cloth not only provides heat preservation and insulation to the scraping and moxibustion device, but also can adjust the burning speed and absorb the moxa oil in the moxa smog that overflows through the enclosure cloth. Only a small amount of moxa oil smog overflows through the through-cavity of the tip during use, and the air in the environment can maintain comfort. A plurality of scraping and moxibustion devices can be connected into a long line or a surface through the hanging members to conduct the moxibustion simultaneously, so that the moxibustion effect is more comprehensive and more obvious. In the practice of scraping and moxibustion, there have been individual cases that have shown positive therapeutic effects on the treatment of facial darkness, pigmentation, hair oil, excessive dandruff, blood loss, early white hair, hair loss, facial paralysis, neurasthenia, insomnia, etc. The handheld multi-tip scraping and moxibustion device allows more people to participate in the therapeutic practice, and an answer to whether it can finally cure mental illnesses remains to be seen through practice.

The moxibustion method is one of the external physiotherapy methods of traditional Chinese medicine, and can play a role in treating and preventing diseases. As the patient experiences a comfortable feeling during the treatment, it is a very popular treatment method among patients. The treatment and health maintenance by the moxibustion method is an embodiment of a "comprehensive effect" according to the theory and practice of traditional Chinese medicine. At present, the state and society are paying more and more attention to traditional Chinese medicine, and various moxibustion devices have been developed, such as that described in CN 203342032 U, in which a multi-acupoint adjustment moxibustion device comprises a moxibustion tube, a support disc, a fixed flexible pipe and a fixing belt. The support disc is assembled to a front end of the fixed flexible pipe, and a rear end of the fixed flexible pipe is fixed with the moxibustion tube. The moxibustion device from CN 203342032 U uses a multi-moxibustion tube structure, and the moxibustion can be conducted to 1 to 4 acupoints at the same time. The moxibustion device from CN 203342032 U uses the fixed flexible pipe to control the position of the moxibustion tube. The distance between the moxibustion tube and the acupoint can be flexibly adjusted, and meanwhile, the fixing belt can fix the moxibustion device to a patient, without the need for a specially-assigned person to hold the device, thereby saving manpower.

However, the existing moxibustion device has a complicated structure and a high manufacturing cost, and moxibustion can only be conducted locally without the function of scraping. Moreover, the adjustment operation to the moxibustion position for different acupoints is inconvenient, and further, the physiotherapy effect and efficiency are not good. Additionally, the existing handheld moxibustion device can only be used in an moxibustion application, and cannot be effectively used in application to sites such as the head due to hair acting as a barrier that prevents access by the device to the scalp.

In order to overcome the problems described above, a handheld multi-tip scraping and moxibustion device has been developed.

SUMMARY OF THE INVENTION

The present invention aims to solve the technical problem by providing a handheld multi-tip scraping and moxibustion device, which is suitable for moxibustion and the scraping therapy principle of traditional Chinese medicine, effectively combining practical concepts of moxibustion, scraping therapy, user convenience, and the like. The device features simplicity and practicality, ease of use, low production costs, and a wide range of applications, and has a structure applicable for a full-body scraping and moxibustion process such that the device can gradually spread heat and air to warm and soothe the body during scraping and moxibustion, which makes patients feel comfortable. Therefore, the handheld multi-tip scraping and moxibustion device is a product of technical, practical and economical superiority.

In order to achieve the objects above, the present invention adopts the following technical solutions:
 a handheld multi-tip scraping and moxibustion device comprising:
 a plurality of pushing and scraping heat-conducting and air-guiding tips distributed on a panel each having a through-cavity; and
 a moxa burning chamber communicating with the through-cavity to enable heat energy and evaporated moxa smog or aromatherapy essential oil in the moxa burning chamber to be discharged gradually through the pushing and scraping heat-conducting and air-guiding tips.

In one or more embodiments of the present invention, the pushing and scraping heat-conducting and air-guiding tips comprise a first set of tips located in a middle portion of the panel and a second set of tips located around the first set of tips. The first set of tips have a height that is less than that of the second set of tips to form a multi-layered stepped air discharge.

In one or more embodiments of the present invention, the moxa burning chamber is formed by the panel, a side enclosure wall connected to an edge of the panel and a cover body detachably assembled to the side enclosure wall, and the moxa burning chamber is provided with a plurality of hanging members at an outer side of the moxa burning chamber. In one or more embodiments of the present invention, the side enclosure wall and the cover body are both provided with a plurality of through-holes. In one or more embodiments of the present invention, the pushing and scraping heat-conducting and air-guiding tips have a circular tubular shape, an elliptical tubular shape or a polygonal tubular shape.

A handheld multi-tip scraping and moxibustion device is provided, which belongs to the same concept as the above, comprising:
 a plurality of pushing and scraping heat-conducting and air-guiding tips distributed on a panel each having a through-cavity;
 a moxa burning chamber formed by the panel, a side enclosure wall and a cover body and communicating with the through-cavity to enable heat energy and evaporated moxa smog or aromatherapy essential oil in the moxa burning chamber to be discharged gradually through the pushing and scraping heat-conducting and air-guiding tips; and
 an enclosure cloth detachably assembled to an outer side of the moxa burning chamber.

In one or more embodiments of the present invention, the panel, the side enclosure wall, the cover body and the pushing and scraping heat-conducting and air-guiding tip are all made of a metal material. In one or more embodiments of the present invention, the metal material is stainless steel, copper or titanium material.

Compared with the existing devices described in background section, the present invention has the following beneficial effects.

By adopting the technical solutions above, the design is suitable for moxibustion and the scraping therapy principle of traditional Chinese medicine, effectively combining practical concepts of moxibustion, scraping therapy, user convenience, and the like. The device features simplicity and practicality, ease of use, low production costs, and wide range of applications, and has a structure applicable for a full-body scraping and moxibustion process such that the device can gradually spread heat and air to warm and soothe the body during scraping and moxibustion, which makes people feel comfortable. Therefore, the handheld multi-tip scraping and moxibustion device is a product of technical, practical and economical superiority.

Both scraping and moxibustion are conducted synchronously to different acupoints of the human body according to physiotherapy requirements by the pushing and scraping motions of the heat-conducting and air-guiding tips. As a result of the length of the outer tips being less than that of the inner tips, a multi-layered stepped air discharge can be achieved so as to provide a wider contact surface between an air discharge surface and a surface of the human body surface, which improves the application efficiency.

Furthermore, when the moxibustion needs to be conducted to the head, the hairs can be pushed aside by the pushing and scraping heat-conducting and air-guiding tips, allowing the heat energy and evaporated moxa smog or aromatherapy essential oil to be directly delivered to the scalp. The side enclosure wall and the cover body are both provided with a plurality of through-holes, and a plurality of positions for discharging air are provided for selection and use.

Secondly, when the handheld multi-tip scraping and moxibustion device is operated in a burning mode, the enclosure cloth can be arranged on the outer side of the moxa burning chamber such that the smog gas is slowly discharged from the moxa burning chamber in an orientation that is fixed by the pushing and scraping heat-conducting and air-guiding tips. A control rate of a burning air inflow surface can be adjusted through the enclosure cloth, and the structure is compact and practical. The outer side of the moxa burning chamber is provided with a plurality of hanging members which can be secured by a rope or connected to other fixing structures to improve the convenience of operating the device.

In addition, an enamel layer is added on the outer surface of the panel pushing and scraping heat-conducting and air-guiding tip so as to prevent the human body from direct contact with the metal element, which is suitable for individuals with an allergy to certain metals.

The invention of the handheld multi-tip scraping and moxibustion device solves the problems described in the background section. The fixed acupoint moxibustion is available, especially the moxibustion to the five acupoints of Baihui and Sishencong at the same time. When the fixed acupoint moxibustion is conducted, the scraping and moxibustion device is fixed by an elastic tape to an individual so that the individual is able to walk as usual. Alternatively, the scraping and moxibustion device can also be held as a comb to conduct the scraping and moxibustion to the vertex and face. The functions of scraping therapy comprising blood dredging, diaphoresis and activation of collaterals are combined with the moxibustion through the present invention so as to produce a new therapy: Scraping and moxibustion. The searching of collaterals, scraping and moxibustion can be conducted throughout the body, with amazing therapeutic effects. The heat energy and the moxa smog are transmitted to the skin through the tip (more specifically by through-cavity that is internally provided in the tip), and the heat energy makes the subject feel pleasant and comfortable when scraping and moxibustion are performed. In the invention, an enclosure cloth is used for covering the device such that only a tip surface of the device is exposed. The enclosure cloth not only provides heat preservation and insulation to the scraping and moxibustion device, but also can be used to adjust the burning speed and absorb the moxa oil in the moxa smog that overflows through the enclosure cloth. Only a small amount of moxa oil smog overflows through the through-cavity of the tip during use, and the air in the environment can be used to maintain comfort. A plurality of scraping and moxibustion devices can be connected into a long line or a surface through the hanging members to conduct the moxibustion simultaneously, so that the moxibustion effect is more comprehensive and more obvious. In the practice of moxibustion, obvious therapeutic effects of different degrees are generated to treat facial darkness, pigmentation, hair oil, excessive dandruff, blood loss, early white hair, hair loss, facial paralysis, neurasthenia, insomnia, etc.

DETAILED DESCRIPTION

Figure 1:
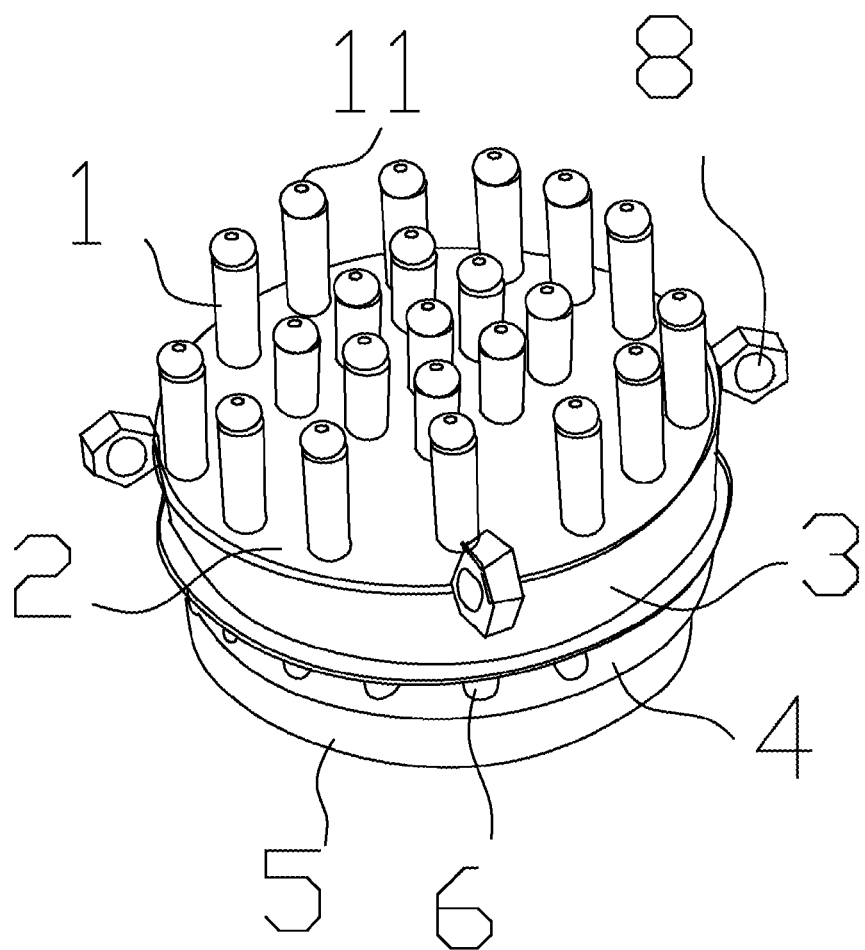
FIG. 1 is a perspective view of a handheld multi-tip scraping and moxibustion device according to one embodiment of the present invention.
Figure 2:
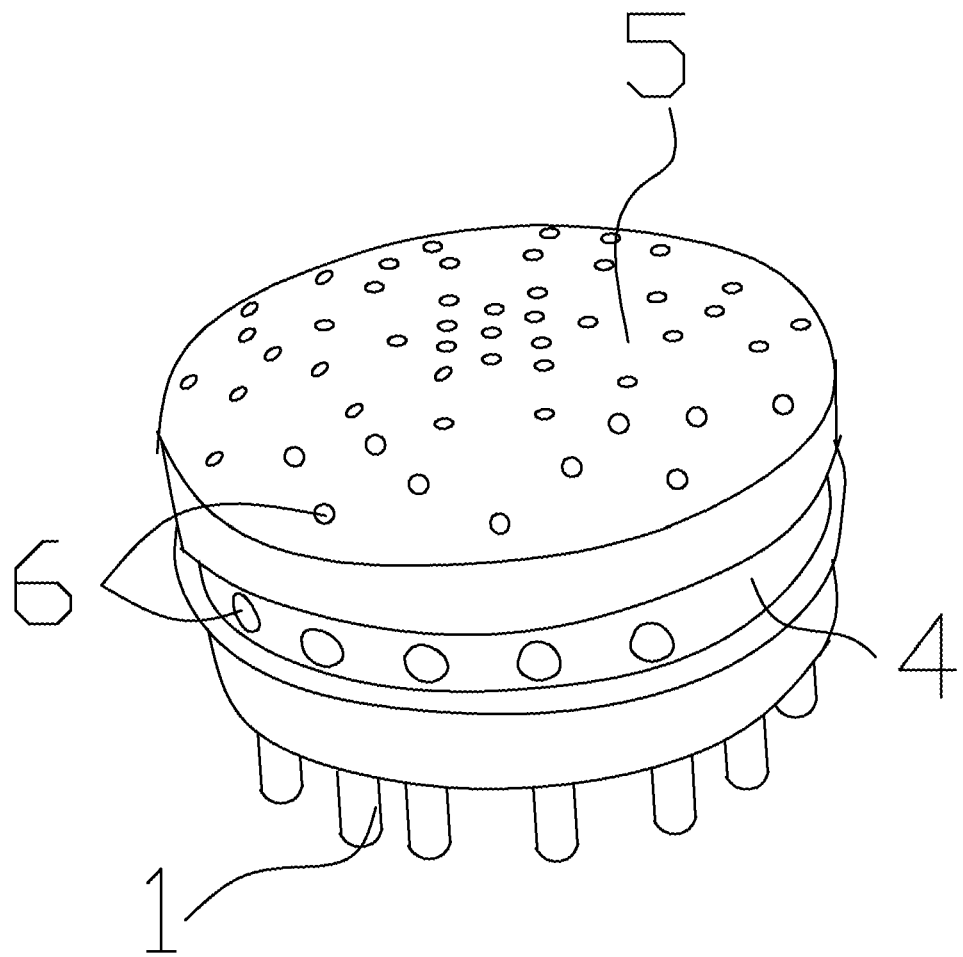
FIG. 2 is a perspective view of the handheld multi-tip scraping and moxibustion device from another perspective according to one embodiment of the present invention.
Figure 3:
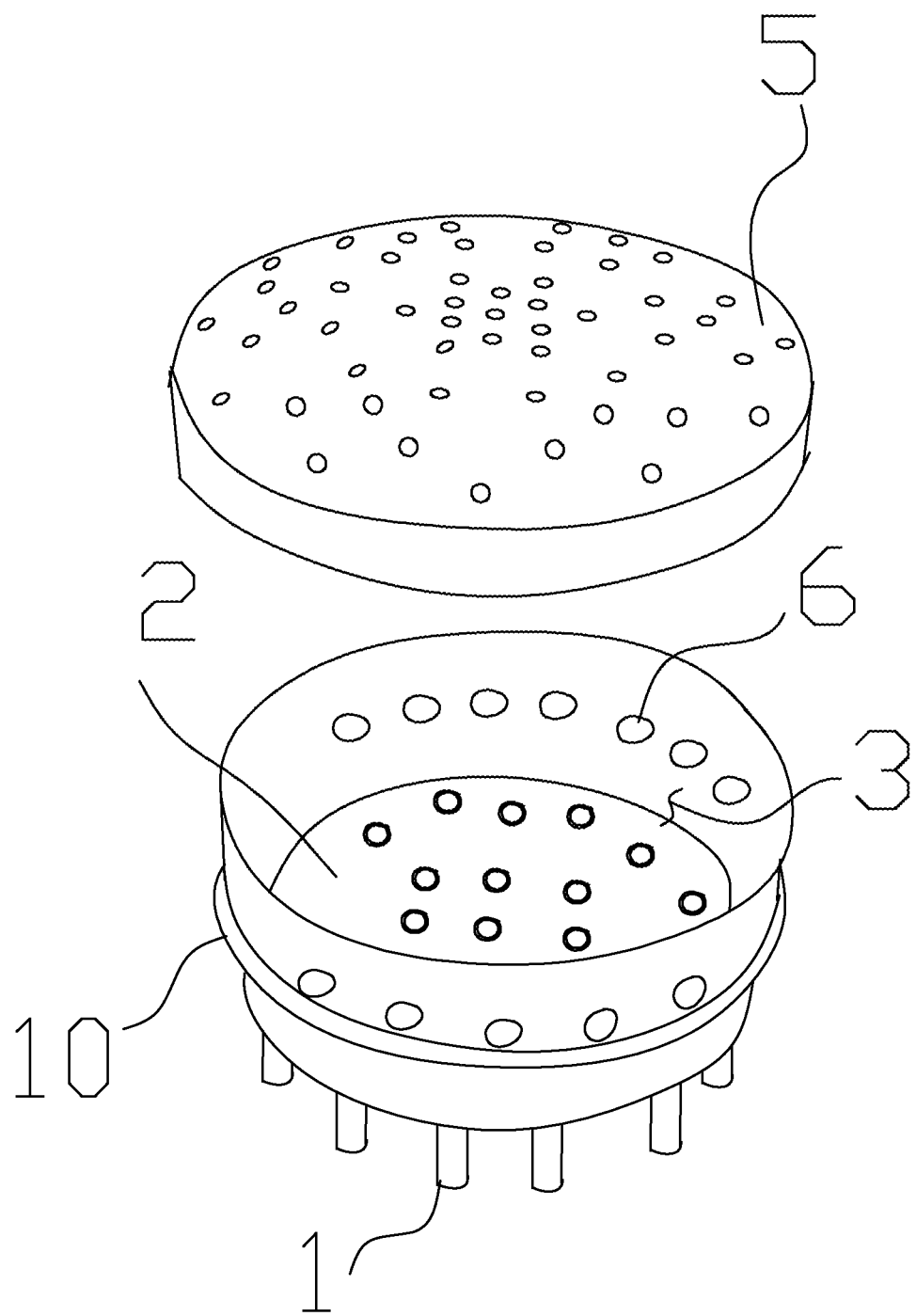
FIG. 3 is an exploded perspective view of the handheld multi-tip scraping and moxibustion device, which more clearly illustrates the internal structure of the handheld multi-tip scraping and moxibustion device according to one embodiment of the present invention.

To facilitate understanding and description, the present invention is further described in detail hereinafter with reference to the accompanying drawings and specific embodiments, but is not limited to the embodiments described herein.

Referring to FIGS. 1-4, a preferred embodiment of the present invention provides a handheld multi-tip scraping and moxibustion device, which comprises a plurality of pushing and scraping heat-conducting and air-guiding tips 1, a panel 2, a moxa burning chamber 3, a side enclosure wall 4, a cover body 5, and other components. The pushing and scraping heat-conducting and air-guiding tips 1 are distributed on the panel 2 and each of the pushing and scraping heat-conducting and air-guiding tips 1 has a through-cavity 11.

The moxa burning chamber 3 is fluidly coupled with each of the through-cavities 11 to enable the hot air in the moxa burning chamber 3 to be slowly released for use via each of the through-cavities 11. The pushing and scraping heat-conducting and air-guiding tips 1 comprise a first set of tips 101 located in a middle portion of the panel 2 and a second set of tips 102 located around the first set of tips 101, wherein the first set of tips 101 have a height that is less than that of the second set of tips 102 so as to form a multi-layered stepped air discharge. An end portion of at least one of the pushing and scraping heat-conducting and air-guiding tips can be arranged in a spherical shape, as shown in FIG. 1.

The moxa burning chamber 3 is formed by the panel 2, the side enclosure wall 4 connected to an edge of the panel 2, and a cover body 5 detachably assembled to the side enclosure wall 4. The side enclosure wall 4 and the cover body 5 are both provided with a plurality of through-holes 6. The shape of the pushing and scraping heat-conducting and air-guiding tip 1 is not specifically defined, and can be made in a circular tubular shape, an elliptical tubular shape or a polygonal tubular shape. The air can also be discharged through the through-hole 6, so that a plurality of positions for discharging air are provided for selection and use.

Figure 4:
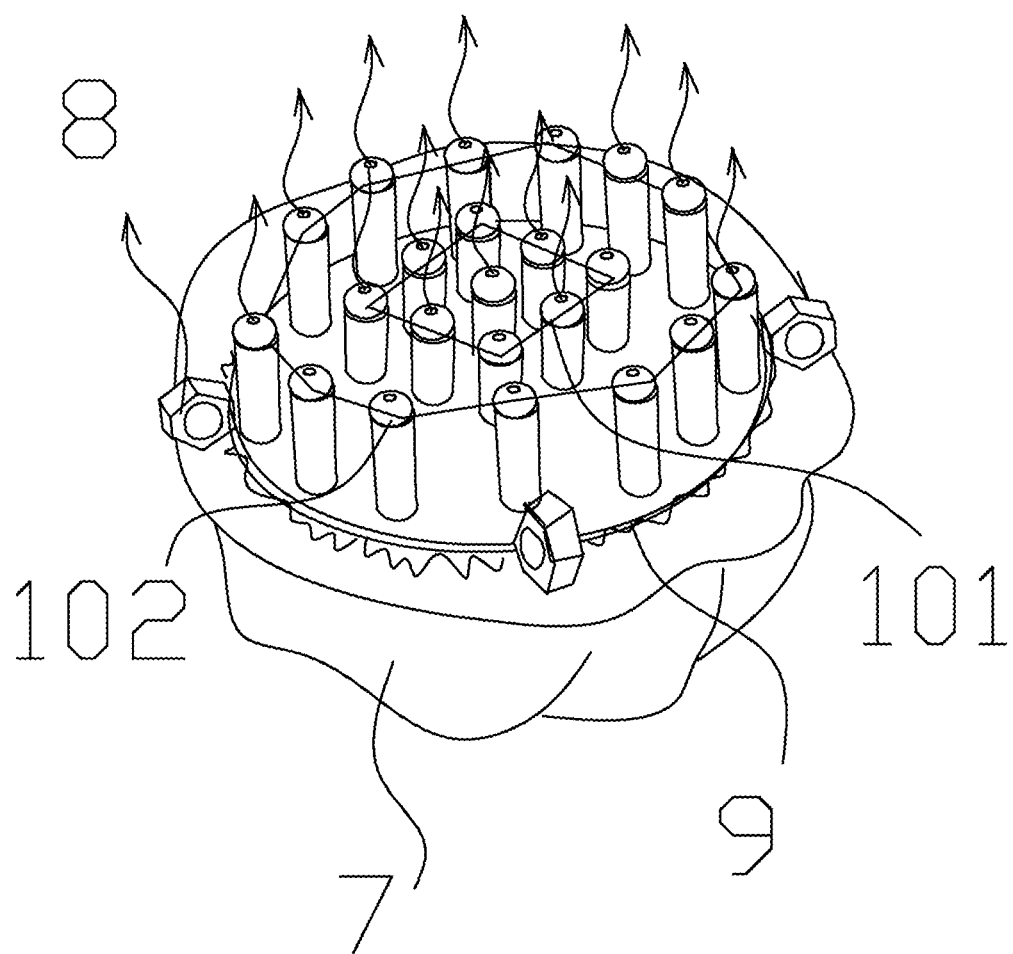
FIG. 4 is a perspective view of the handheld multi-tip scraping and moxibustion device when in use according to one embodiment of the present invention.

The moxa burning chamber 3 is detachably provided at an outer side thereof with an enclosure cloth 7 and with an elastic band 9 for securing the enclosure cloth 7 to the moxa burning chamber 3. The side enclosure wall 4 is provided with an extension edge 10 at an outer side thereof, and the elastic band 9 is buckled on the extension edge 10 to make the elastic band 9 more difficult to come loose. The moxa burning chamber 3 is provided with a plurality of hanging members 8 at an outer side. As shown in FIGS. 1 and 4, a portion of each of the hanging members 8 may extend in a vertical direction beyond the surface of the panel 2. When the handheld multi-tip scraping and moxibustion device is operated in a burning mode, the enclosure cloth 7 can be arranged on the outer side of the moxa burning chamber 3 such that the smog gas is slowly discharged from the moxa burning chamber 3 in an orientation that is fixed by the pushing and scraping heat-conducting and air-guiding tips 1. A control rate of an air inflow surface of the device can be adjusted through the enclosure cloth 7, and the structure is compact and practical. The outer side of the moxa burning chamber 3 is provided with a plurality of hanging members 8 which can be secured by a rope or connected to other fixing structures to improve the convenience of operating the device.

The panel 2, the side enclosure wall 4, the cover body 5 and the pushing and scraping heat-conducting and air-guiding tips 1 described above may be made of a metal material which may preferably be stainless steel, copper or titanium.

With reference to the above descriptions and all the drawings, the use and principle of the present invention are described as follows. Firstly, a moxa roll (not shown in the drawings) can be lighted and placed in the moxa burning chamber 3. According to physiotherapy requirements, both scraping and moxibustion are conducted at the same time to acupoints by the pushing and scraping heat-conducting and air-guiding tips 1. Due to the length of the outer tips 102 being greater than that of the inner tips 101, a multi-layered stepped air discharge can be achieved so as to have a wider contact surface between an air discharge surface and a human body surface, which improves the application efficiency. The whole design is suitable for moxibustion and the scraping therapy principle of traditional Chinese medicine, effectively combining practical concepts of moxibustion, scraping therapy, user convenience, and the like. The device features simplicity and practicality, ease of use, low production costs, and a wide range of applications. The device has a structure applicable for a full-body scraping and moxibustion process such that the device can gradually spread heat and air to warm and soothe the body during scraping and moxibustion, which makes people feel comfortable. Therefore, the handheld multi-tip scraping and moxibustion devices are the products of technical, practical and economical superiority.

Through the description to the structure and principle above, those skilled in the art should understand that the present invention is not limited to the specific embodiments described above, and the improvements and substitutions known in the art based on the present invention shall all fall within the protection scope of the present invention, and shall be defined by all the claims.

What is claimed is:

1. A handheld multi-tip scraping and moxibustion device, comprising:
    a plurality of pushing and scraping heat-conducting and air-guiding tips; and
    a moxa burning chamber formed in part by a panel with a first surface facing towards the plurality of tips,
        wherein the plurality of pushing and scraping heat-conducting and air-guiding tips are distributed on the panel and protrude from the first surface of the panel in a first direction away from the moxa burning chamber, each tip having a through-cavity passing through the tip into the moxa burning chamber, whereby the plurality of tips are configured to provide force exerted by a human operator on an affected part of a human body,
        wherein the moxa burning chamber is fluidly coupled to the through-cavity of each tip to enable heat energy and evaporated moxa smog or aromatherapy essential oil in the moxa burning chamber to be discharged through each of the pushing and scraping heat-conducting and air-guiding tips, and
        wherein each pushing and scraping heat-conducting and air-guiding tip is made of a heat-conducting material, the device further comprising:
    a plurality of hanging members attached to the moxa burning chamber, wherein a portion of each of the hanging members extends in the first direction beyond the first surface of the panel.

2. The handheld multi-tip scraping and moxibustion device of claim 1, wherein the pushing and scraping heat-conducting and air-guiding tips comprise a first set of tips located in a middle portion of the panel and a second set of tips located around the first set of tips, wherein the first set of tips has a height less than that of the second set of tips to form a multi-layered stepped air discharge.

3. The handheld multi-tip scraping and moxibustion device of claim 2, wherein the moxa burning chamber is formed by the panel, a side enclosure wall connected to an edge of the panel and a cover body detachably assembled to the side enclosure wall.

4. The handheld multi-tip scraping and moxibustion device of claim 3, wherein the side enclosure wall and the cover body each comprise a plurality of through-holes.

5. The handheld multi-tip scraping and moxibustion device of claim 4, wherein the pushing and scraping heat-conducting and air-guiding tips each have a circular tubular shape, an elliptical tubular shape or a polygonal tubular shape.

6. The handheld multi-tip scraping and moxibustion device of claim 1, wherein the pushing and scraping heat-conducting and air-guiding tips each have an end portion with a spherical shape.

7. The handheld multi-tip scraping and moxibustion device of claim 1, wherein the heat-conducting material is a metal material.

8. The handheld multi-tip scraping and moxibustion device of claim 7, wherein the metal material is coated with an enamel layer so as to prevent the affected part of the human body from direct contact with the metal material.

9. A handheld multi-tip scraping and moxibustion device, comprising:
    a plurality of pushing and scraping heat-conducting and air-guiding tips;
    a moxa burning chamber formed in part by a panel with a first surface facing towards the plurality of tips; and
    an enclosure cloth,
    wherein the plurality of pushing and scraping heat-conducting and air-guiding tips are distributed on the panel and protrude from the first surface of the panel in a first direction away from the moxa burning chamber, each tip having a through-cavity passing through the tip into the moxa burning chamber, whereby the plurality of tips are configured to provide force exerted by a human operator on an affected part of a human body,
    wherein the moxa burning chamber is formed by the panel, a side enclosure wall and a cover body and is fluidly coupled to the through-cavity of each tip to enable heat energy and evaporated moxa smog or aromatherapy essential oil in the moxa burning chamber to be discharged through each of the pushing and scraping heat-conducting and air-guiding tips, and
    wherein the enclosure cloth is detachably attached to an outer side of the moxa burning chamber, and is configured to adjust a control rate of a burning air inflow surface such that a burning speed in the moxa burning chamber is controlled, the device further comprising:
    a plurality of hanging members attached to the moxa burning chamber, wherein a portion of each of the hanging members extends in the first direction beyond the first surface of the panel.

10. The handheld multi-tip scraping and moxibustion device of claim 6, wherein the panel, the side enclosure wall, the cover body and the pushing and scraping heat-conducting and air-guiding tips are all made of a metal material.

11. The handheld multi-tip scraping and moxibustion device of claim 10, wherein the metal material is stainless steel, copper or a titanium material.

12. The handheld multi-tip scraping and moxibustion device of claim 9, wherein the pushing and scraping heat-conducting and air-guiding tips each have an end portion with a spherical shape.

* * * * *